United States Patent [19]

Blum et al.

[11] 4,361,501

[45] Nov. 30, 1982

[54] PREPARATION OF VANADIUM PHOSPHORUS CATALYSTS USING A MIXED PHOSPHORUS SOURCE

[75] Inventors: Patricia R. Blum, Macedonia; Ernest C. Milberger, Solon; Noel J. Bremer, Stow; Dennis E. Dria, Shaker Hts, all of Ohio

[73] Assignee: The Standard Oil Company, Cleveland, Ohio

[21] Appl. No.: 220,629

[22] Filed: Dec. 29, 1980

[51] Int. Cl.$^3$ .............................................. B01J 27/14
[52] U.S. Cl. .................................... 252/435; 252/437
[58] Field of Search ................................ 252/435, 437

[56] References Cited

U.S. PATENT DOCUMENTS

| | | | |
|---|---|---|---|
| 2,773,921 | 12/1956 | Rylander et al. | 260/683.15 |
| 3,238,254 | 3/1966 | Kerr | 260/530 |
| 3,474,041 | 10/1969 | Kerr | 252/437 X |
| 3,907,707 | 9/1975 | Roffelson et al. | 252/437 |
| 4,013,586 | 3/1977 | Dolan et al. | 252/437 |
| 4,016,105 | 4/1977 | Kerr | 252/437 |
| 4,018,709 | 4/1977 | Barone et al. | 252/435 |
| 4,043,943 | 8/1977 | Schneider | 252/437 |
| 4,149,992 | 4/1979 | Mount | 252/435 |
| 4,179,404 | 12/1979 | Barone | 252/435 |

*Primary Examiner*—Delbert E. Gantz
*Assistant Examiner*—William G. Wright
*Attorney, Agent, or Firm*—Joseph G. Curatolo; Herbert D. Knudsen; Larry W. Evans

[57] ABSTRACT

The present invention provides a process for the preparation of oxidation catalysts containing mixed oxides of vanadium and phosphorus, which catalysts are particularly effective in the oxidation of n-butane, n-butenes, 1,3-butadiene or a mixture thereof with molecular oxygen or an oxygen-containing gas in the vapor phase to produce high yields of maleic anhydride with good selectivity. A vanadium compound is introduced into a liquid medium, a mixed phosphorus component comprising orthophosphoric acid and pyrophosphoric acid is added to the liquid medium, reduction of at least a portion of the vanadium to a +4 valence state is effected either prior to or subsequent to the addition of the mixed phosphorus component, and the resulting vanadium-phosphorus oxide catalyst precursor is recovered, dried and calcined.

15 Claims, No Drawings

PREPARATION OF VANADIUM PHOSPHORUS CATALYSTS USING A MIXED PHOSPHORUS SOURCE

BACKGROUND OF THE INVENTION

This invention relates to a process for preparing catalysts useful in the production of dicarboxylic acid anhydrides by the oxidation of hydrocarbons. More particularly it is directed to the preparation of catalysts suitable for producing maleic anhydride from 4-carbon atom hydrocarbons, such as n-butane, n-butenes, 1,3 butadiene or a mixture thereof.

Catalysts containing vanadium and phosphorus oxides have been used in the oxidation of 4-carbon atom hydrocarbons, such as n-butane, n-butenes, 1,3 butadiene or mixtures thereof with molecular oxygen or oxygen-containing gas to produce maleic anhydride. Conventional methods of preparing these catalysts involve combining a vanadium compound, a phosphorus compound, and if desired, promoter element compounds in a reducing medium under conditions which will provide vanadium in a valence state below +5 to form catalyst precursors capable of being converted to an oxide. The catalyst oxide precursor is then recovered and calcined to provide active catalytic material.

It has been taught in the art that various pentavalent and trivalent phosphorus compounds are satisfactory phosphorus components for use in the preparation of mixed vanadium phosphorus oxide catalysts. Orthophosphoric acid has been designated by some in the art as a preferred component.

U.S. Pat. No. 3,238,254 to Kerr lists the use of various phosphorus compounds such as metaphosphoric acid, triphosphoric acid, pyrophosphoric acid, orthophosphoric acid, phosphorus pentoxide, phosphorus oxyiodide, ethyl phosphate, methyl phosphate, amine phosphate, phosphorus pentachloride, phosphorus trichloride, phosphorus oxybromide, and the like, in the preparation of catalysts containing the mixde oxides of vanadium and phosphorus.

U.S. Pat. No. 3,474,041 to Kerr contains the above disclosure, and additionally discloses that vanadium phosphorus catalysts may be reactivated and stabilized by adding to the catalyst an organophosphorus compound.

U.S. Pat. Nos. 3,907,707 to Raffelson et al., 4,149,992 to Mount et al. and 4,179,404 to Barone disclose the preparation of vanadium phosphorus oxide catalysts using trivalent phosphorus compounds such as orthophosphorous acid, pyrophosphorous acid, metaphosphorous acid and hypophosphorous acid. Other phosphorus sources may include phosphorus trioxide and organic phosphites. A pentavalent phosphorus compound additionally could be utilized.

U.S. Pat. No. 4,043,943 discloses the preparation of the vanadium phosphorus oxide catalyst in a liquid organic medium, preferably anhydrous, wherein the vanadium compound is reduced and solvated by gaseous HCl followed by reaction with the phosphorus compound.

The preparation of oxidation catalysts containing the mixed oxides of vanadium and phosphorus is disclosed in copending U.S. Ser. No. 106,786, assigned to our common assignee, wherein a vanadium compound is at least partially solubilized in an organic liquid medium capable of reducing at least a portion of the vanadium to a +4 valence state, and unsolubilized vanadium having a particle size larger than about 0.1 mm diameter is removed from the medium before addition of a phosphorus-containing compound.

The preparation of such catalysts is disclosed in copending U.S. Ser. No. 146,971, assigned to our common assignee, wherein partial reduction of a pentavalent vanadium compound is effected in the presence of a phosphorus compound in an organic liquid medium capable of reducing the vanadium.

U.S. Pat. No. 4,013,586 to Dolan et al. discloses the preparation of vanadium phosphorus oxide catalysts using organo phosphonates as the source of phosphorus. A pentavalent phosphorus compound additionally could be utilized.

DISCLOSURE OF THE INVENTION

We have found that vanadium phosphorus mixed oxide catalysts having unexpectedly increased activity and enhanced processibility can be prepared using a mixed pentavalent phosphorus source of both orthophosphoric acid and pyrophosphoric acid. Catalysts thus prepared exhibit higher activity and selectivity to the preparation of maleic anhydride from four carbon atom hydrocarbons such as n-butane at equivalent operating temperatures.

Catalyst precursors produced according to the process of the present invention exhibit enhanced processibility into formed catalysts suitable for commercial uses. Whereas catalyst precursors prepared using orthophosphoric acid alone as the phosphorus source produce fine powders, catalyst precursors prepared according to the process of the invention, using a mixed ortho/pyro-phosphoric acid source as the phosphorus component, form coarser particles which agglomerate more readily when formed into commercially usable catalysts.

It is therefore an object of the invention to provide a process for preparing vanadium and phosphorus oxide-containing oxidation catalysts.

It is a further object of the invention to provide a process for preparing vanadium and phosphorus oxide-containing catalysts useful for the oxidation of 4-carbon atom hydrocarbons to produce maleic anhydride, which catalysts exhibit high yields and selectivity to maleic anhydride.

It is a further object of the invention to provide a process of preparing vanadium and phosphorus oxide-containing catalysts exhibiting enhanced commercial processibility.

These and other objects, together with the advantages thereof over known methods, which shall be apparent from the specification which follows, are accomplished by the invention as hereinafter described and claimed.

In general the process of the present invention comprises the steps of (a) introducing a pentavalent vanadium-containing compound into a liquid medium capable of reducing the valence state of said vanadium;

(b) effecting reduction of at least a portion of said vanadium to a valence state of +4;

(c) adding a mixed phosphorus component to said medium to form a catalyst precursor precipitate;

(d) recovering the catalyst precursor precipitate;

(e) drying the catalyst precursor precipitate;

(f) calcining the catalyst precursor precipitate.

Another embodiment of the process of the present invention comprises the steps of (a) introducing a pentavalent vanadium-containing compound into a liquid medium capable of at least partially solubilizing the vanadium and of reducing the valence state of said vanadium;

(b) effecting reduction of at least a portion of said vanadium to a valence state of about +4;

(c) removing unsolubilized vanadium-containing compounds having a particle size greater than about 0.1 mm diameter;

(d) adding a mixed phosphorus component to the reaction medium resulting from step (c) to form a catalyst precursor precipitate;

(e) recovering the catalyst precursor precipitate;

(f) drying the catalyst precursor precipitate; and (g) calcining the catalyst precursor precipitate.

Yet another embodiment of the process of the present invention comprises the steps of (a) introducing a pentavalent vanadium compound and a mixed phosphorus component into a liquid medium;

(b) effecting reduction of at least a portion of the vanadium to a valence state of about +4 while in the presence of the mixed phosphorus component to form a vanadium-phosphorus mixed oxide precursor;

(c) recovering the vanadium phosphorus mixed oxide catalyst precursor;

(d) drying said catalyst precursor; and (e) calcining the catalyst precursor.

The liquid medium capable of reducing the valence of pentavalent vanadium may comprise an aqueous medium containing reducing agents, a mixed aqueous/organic liquid medium, or an essentially organic liquid medium.

The catalysts prepared by the above process are particularly effective in the oxidation of 4-carbon atom hydrocarbons such as n-butane, n-butenes, 1,3 butadiene or mixtures thereof with molecular oxygen or an oxygen-containing gas in the vapor phase to produce high yields of maleic anhydride with high selectivity. Essentially all the product produced in this oxidation process is maleic anhydride, with only minor amounts of lower acids being detected.

DETAILED DESCRIPTION OF THE INVENTION

In the process for the preparation of an oxidation catalyst containing the mixed oxides of vanadium and phosphorus, a vanadium compound, particularly a pentavalent vanadium compound, is introduced into a liquid medium capable of reducing the valence state of the vanadium. Suitable vanadium compounds containing pentavalent vanadium include: vanadium pentoxide or vanadium salts, such as ammonium metavanadate and vanadium oxytrihalides. Vanadium pentoxide is preferred.

In one embodiment of the invention, the pentavalent vanadium containing compound is at least partially solubilized in the liquid medium. To aid in solubilizing the vanadium, it is preferred that the vanadium-containing compound which is introduced into the liquid medium have a small particle size, and methods for further reducing particle size of the vanadium compound while in the liquid medium, such as by ball milling the initial suspension of vanadium in the liquid medium, may be employed.

The liquid medium used in the process of the present invention may comprise an aqueous medium which contains reducing agents including but not limited to HCl or HBr, finely divided or colloidal metals, or organic reducing agents such as alcohols, acids, aldehydes, ethers, ketones and the like. The liquid medium preferably comprises an organic liquid capable of reducing at least a portion of the vanadium to a valence state of +4. The organic liquid medium may comprise alcohols, carboxylic acids, aldehydes, ketones, ethers, epoxides, oxygenated olefinic organic liquids, halogenated olefinic organic liquids and mixtures thereof, among others. It is preferred that the liquid medium comprise and be maintained as an essentially anhydrous organic liquid. The liquid medium is preferably a solvent for and is relatively inert towards the mixed phosphorus component.

After the pentavalent vanadium compound is introduced into the liquid medium, reduction of the vanadium is effected either prior to or subsequent to the addition of the mixed phosphorus component to the liquid medium. The reduction is effected preferably by heating the resulting reaction medium, with stirring if desired. Preferred vanadium and phosphorus oxide catalysts for the oxidation of 4-carbon atom hydrocarbons to maleic anhydride contain vanadium in an average valence state of about +3.5 to about +4.6. This average valence state is achieved when at least a portion of the pentavalent vanadium introduced into the reaction mixture is reduced to the +4 state. The average valence state of the vanadium is reduced preferably to about +4.1.

After partial reduction of the vanadium, in one embodiment of the invention, unsolubilized vanadium-containing compounds are removed from the reaction mixture. While the unsolubilized vanadium-containing compounds generally contain some portion of vanadium in a valence state less than +5, the greater portion of vanadium present remains in a +5 valence state. Although it is preferred in this embodiment to remove all unsolubilized vanadium-containing compounds from the liquid medium after effecting reduction of the vanadium, removing all such unsolubilized vanadium-containing compounds having a particle size greater than about 0.1 mm diameter, results in the production of catalysts exhibiting excellent activity for the preparation of maleic anhydride, producing high yields at high selectivity. In a preferred mode of this embodiment of the process of the invention, all unsolubilized vanadium-containing compounds having a particle size greater than about 0.04 to about 0.06 mm diameter are removed. Removal is achieved by conventional means, such as filtration, centrifugation, decantation and the like. After removal of unsolubilized vanadium-containing compounds from the liquid reaction medium, in this embodiment of the invention, the phosphorus component is added to the reaction medium.

The mixed pentavalent phosphorus component according to the present invention comprises a mixture of orthophosphoric acid and pyrophosphoric acid. Optionally, minor amounts of higher polyphosphoric acid may be included. The mixture should comprise about 45 to 90 percent orthophosphoric acid, 10 to 50 percent pyrophosphoric acid, and 0 to 10 percent triphosphoric acid and higher polyphosphoric acids, percentages being based upon weight of total phosphoric acids. As hydrolysis is a factor in determining the ratio of orthophosphoric acid to pyrophosphoric acid when present in aqueous solution, the above weight ratios are significant provided an extended period of hydrolysis has not occurred to convert the pyrophosphoric acid and higher polyphosphoric acids to the orthophosphoric form.

The mixed phosphorus component is preferably added to the reaction medium in the form of a solution of the phosphorus component in either a component of the liquid reaction medium, or in a liquid capable of yielding the phosphorus component to the liquid reaction medium. After addition of the phosphorus component to the liquid reaction medium, it is preferable to heat the liquid reaction medium, with stirring, if necessary.

In other embodiments of the invention, the phosphorus component, as described above, is added to the liquid medium either before reduction of the pentavalent vanadium substantially occurs, or after such reduction, with no pre-reduction filtration of unsolubilized vanadium compounds. When reduction of the vanadium is effected in the presence of the phosphorus component, the resulting solids dispersed in the liquid medium include the vanadium-phosphorus mixed oxide precursors, to be recovered, dried and calcined. After the catalyst precursor is formed, it is recovered from the reaction medium by conventional methods including evaporation, filtration, centrifugation and decantation.

The catalyst precursor or catalyst precursor precipitate is dried and thereafter calcined at a temperature of 250° C. to 600° C., preferably in the presence of an oxygen-containing gas.

It is within the scope of this invention, to include promoter element-containing compounds in the reaction mixture at a suitable point, either prior to or subsequent to reduction of the vanadium, in order that the catalyst precursor or catalyst precursor precipitate contain the promoter element. Suitable promoters include but are not limited to U, Co, Mo, Fe, Zn, Hf, Zr or mixtures thereof.

Catalysts prepared by this method may exhibit a phosphorus to vanadium ratio of about 0.5:1 to about 3:1. Preferred is a P/V ratio of about 0.9:1 to about 1.3:1.

The catalyst is calcined in an inert atmosphere, air or an oxygen-containing gas at a temperature of 250° C. to 600° C. for a period of up to 5 hours or more. Calcination of the catalyst may be accomplished by heating the catalyst in a mixture of steam and air or air alone over the catalyst at a temperature of about 300° C. to 500° C. for a period of about 1 to 5 hours. The catalyst may also be calcined either in the presence of hydrocarbon, an inert gas, or both.

The hydrocarbon reacted to form maleic anhydride may be n-butane, n-butenes, 1,3-butadiene, or a mixture thereof. Preferred is the use of n-butane or a mixture of hydrocarbons that are produced in refinery streams. The molecular oxygen needed for the reaction to produce maleic anhydride is most conveniently added as air, but synthetic streams containing molecular oxygen are also suitable. In addition to the hydrocarbon and molecular oxygen, other gases may be added to the reactant feed. For example, steam or nitrogen could be added to the reactants.

The ratio of the reactants may vary widely and are not critical. The ratio of molecular oxygen to the hydrocarbon may range from about 3 to about 30 moles of oxygen per mole of hydrocarbon. Preferred oxygen/hydrocarbon ratios are about 4 to about 20 moles of oxygen per mole of hydrocarbon.

The reaction temperature may vary widely and is dependent upon the particular hydrocarbon and catalyst employed. Normally, temperatures of about 250° C. to about 600° C. are employed with temperatures of 350° C. to 500° C. being preferred.

The catalyst may be used alone or a support could be employed. Suitable supports include silica, alumina, Alundum, silicon carbide, titania, boron phosphate, zirconia, and the like. The catalysts may be used in a fixed-bed reactor using tablets, pellets or the like, or in a fluid-bed reactor using catalysts preferably having a particle size of less than about 300 microns. The contact time may be as low as a fraction of a second or as high as 50 seconds. The reaction may be conducted at atmospheric, superatmospheric or subatmospheric pressure.

SPECIFIC EMBODIMENTS OF THE INVENTION

EXAMPLES 1-7

Catalyst having the formula $V_{1.0}P_{1.16}O_x$, where x equals the number of oxygens required to satisfy the valence requirements of the other elements, was prepared from a mixed orthophosphoric/pyrophosphoric acid source according to the following procedure.

About 91 g $V_2O_5$ and about 112 g of a mixed phosphoric acid source containing about 49% orthophosphoric acid, 42% pyrophosphoric acid, 8% triphosphoric acid, and 1% higher polyphosphoric acids was added to about 1.5 liters isobutanol with stirring, and the resulting slurry refluxed for about 16 hours. The slurry was cooled and the catalyst precursor was recovered by filtration. The catalyst precursor was dried for 2 hours at 150° C., was thereafter calcined at 400° C. for 1 hour in air, and was then tabletted to 3/16 inch (0.48 cm) tablets using 3% stearic acid.

COMPARATIVE EXAMPLES 8-11

Catalyst having the formula $V_{1.0}P_{1.16}O_x$ was prepared from an orthophosphoric acid-only phosphorus source according to the following procedure. About 91 g $V_2O_5$ and about 138 g 85% orthophosphoric acid were added to 1.5 liters isobutanol with stirring, and the resulting slurry was refluxed for 16 hours. The cooling, filtration, drying, calcining and pelletting procedures of Examples 1-7 were repeated using the catalyst precursor of Examples 8-11.

COMPARATIVE EXAMPLES 12-15

Catalyst having the formula $V_{1.0}P_{1.16}O_x$ was prepared from an orthophosphoric acid-only phorphorus source according to the following procedure. About 909 g $V_2O_5$ and about 1176 g 100% crystalline orthophosphoric acid were added to about 16 liters isobutanol with stirring, and the resulting slurry was refluxed for 16 hours. The cooling, filtration, drying, calcining and pelletting procedures of Examples 1-7 were repeated using the catalyst precursor of Examples 12-15.

The catalysts described in Examples 1-7 and Comparative Examples 8-15 were used to produce maleic anhydride from butane using a 20 cc fixed-bed reactor consisting of a 38 cm length of stainless steel tubing having an outer diameter of about 1.3 cm and having a full length 0.31 cm axial thermowell. The reactor was heated with a split stainless steel block furnace. Flasks for receiving the product maleic anhydride were mounted in ice water, and tail gases were routed to a Carle Analytical Gas Chromatograph III for analysis. Reaction conditions and results of the tests run are described in Table I. The results are stated in terms as follows:

$$\text{Single Pass Yield} = \frac{\text{Moles of Maleic Anhydride Formed}}{\text{Moles of Butane Fed}} \times 100$$

$$\text{Total Conversion} = \frac{\text{Moles of Butane Reacted}}{\text{Moles of Butane Fed}} \times 100$$

$$\text{Selectivity} = \frac{\text{Single Pass Yield}}{\text{Total Conversion}}$$

As can be seen from the results listed in Table I, vanadium phosphorus oxide containing catalysts prepared according to the process of the invention, utilizing a mixed phosphorus component of orthophosphoric and pyrophosphoric acids in the preparation of the catalysts effect unexpectedly high yields and selectivities of 4-carbon atom hydrocarbons (such as butane) to maleic anhydride as compared to catalysts containing a single phosphorus component preferred by the prior art.

Thus it should be apparent to those skilled in the art that the subject invention accomplishes the objects set forth above. It is to be understood that the subject invention is not to be limited by the examples set forth herein. These have been provided merely to demonstrate operability, and the selection of vanadium compounds, liquid media, promoter element-containing compounds if any, hydrocarbon feedstocks and reaction conditions can be determined from the total specification disclosure provided without departing from the spirit of the invention herein disclosed and described, the scope of the invention including modifications and variations that fall within the scope of the attached claims.

TABLE I

OXIDATION OF n-BUTANE TO MALEIC ANHYDRIDE USING $V_{1.0}P_{1.16}O_x$ CATALYSTS

| | Temperature °C. | % Conversion | Maleic Anhydride % Yield | % Selectivity | Hours On Stream |
|---|---|---|---|---|---|
| Example | | | | | |
| 1 | 403 | 93.3 | 57.6 | 61.8 | 70 |
| 2 | 402 | 90.4 | 55.4 | 61.3 | 88 |
| 3 | 403 | 87.4 | 56.4 | 64.5 | 159 |
| 4 | 403 | 86.7 | 56.6 | 65.3 | 239 |
| 5 | 403 | 85.7 | 56.1 | 65.4 | 287 |
| 6 | 404 | 87.0 | 54.7 | 62.7 | 405 |
| 7 | 403 | 87.1 | 56.4 | 64.7 | 567 |
| Comparative Examples | | | | | |
| 8 | 411 | 82 | 46.7 | 59.6 | 19 |
| 9 | 416 | 86 | 49.7 | 59.0 | 45 |
| 10 | 416 | 89 | 52.4 | 60.2 | 139 |
| 11 | 421 | 89 | 51.8 | 59.1 | 165 |
| 12 | 396 | 77.7 | 48.7 | 62.7 | 50 |
| 13 | 399 | 77 | 50.0 | 65 | 70 |
| 14 | 399 | 74.1 | 49.5 | 66.8 | 186 |
| 15 | 402 | 73.0 | 45.0 | 61.6 | 333 |

We claim:

1. A process for the preparation of oxidation catalysts containing the mixed oxides of vanadium and phosphorus which comprises
    (a) introducing a pentavalent vanadium-containing compound into a liquid medium, capable of reducing the valence state of said vanadium;
    (b) effecting reduction of at least a portion of said vanadium to a valence state of about +4;
    (c) adding a mixed phosphorus component comprising 45-90% by weight orthophosphoric acid and 10-50% by weight pyrophosphoric acid to said medium prior to or subsequent to effecting said reduction to form a catalyst precursor;
    (d) recovering the catalyst precursor;
    (e) drying the catalyst precursor;
    (f) calcining the catalyst precursor.

2. A process as recited in claim 1 wherein said reduction of vanadium is effected in the presence of the mixed phosphorus component.

3. A process for the preparation of an oxidation catalyst containing the mixed oxides of vanadium and phosphorus from at least one pentavalent vanadium-containing compound and a mixed phosphorus component, wherein the pentavalent vanadium is reduced to an average valence state of about +3.5 to about +4.6, including the step of contacting the vanadium with said mixed phosphorus component comprising 45-90% by weight orthophosphoric acid and 10-50% by weight pyrophosphoric acid in a liquid medium.

4. A process for the preparation of oxidation catalysts containing the mixed oxides of vanadium and phosphorus which comprises
    (a) introducing a pentavalent vanadium-compound into a liquid medium capable of at least partially solubilizing the vanadium and of reducing the valence state of said vanadium;
    (b) effecting reduction of at least a portion of said vanadium to a valence state of about +4;
    (c) removing unsolubilized vanadium-containing compounds having a particle size greater than about 0.1 mm diameter;
    (d) adding a mixed phosphorus component comprising 45-90% by weight orthophosphoric acid and 10-50% by weight pyrophosphoric acid to the reaction medium resulting from step (c) to form a catalyst precursor precipitate;
    (e) recovering said catalyst precursor precipitate;
    (f) drying said catalyst precursor precipitate; and
    (g) calcining said precipitate.

5. A process as recited in claims 1, 3 or 4 wherein said liquid medium comprises an organic liquid medium.

6. A process as recited in claim 5 wherein said organic liquid medium is essentially anhydrous.

7. A process as recited in claim 5 wherein said organic liquid medium comprises isobutanol.

8. A process as recited in claims 1, 3 or 4 wherein reduction of said vanadium is effected by heating the vanadium-containing liquid medium.

9. A process as recited in claims 1, 3 or 4 wherein said vanadium-containing compound is vanadium pentoxide.

10. A process as recited in claims 1, 3 or 4 wherein said phosphorus component additionally contains triphosphoric acid up to 10% by weight.

11. A process as recited in claim 1, 3 or 4 wherein said oxidation catalyst is represented by the empirical formula:

wherein

Y=U, Co, Mo, Fe, Zn, Hf, Zr and mixtures thereof; and
a=0.5 to 3.0,
b=0 to about 0.5,
and x is the number of oxygens required to satisfy the valence requirements of the other elements.

12. A process as recited in claims 1, 3 or 4 wherein said oxidation catalyst is represented by the empirical formula $V_1P_{1.16}O_x$.

13. An oxidation catalyst comprising the mixed oxides of vanadium and phosphorus, wherein the average valence state of said vanadium is in the range of +3.5 to +4.6 and the ratio of phosphorus to vanadium is in the range of about 0.5:1 to 3:1, wherein said catalyst is prepared by contacting a vanadium compound with a mixed phosphorus component comprising 45–90% by weight orthophosphoric acid and 10–50% by weight pyrophosphoric acid in a liquid medium.

14. An oxidation catalyst as recited in claim 13 wherein said mixed phosphorus component additionally comprises up to 10% triphosphoric acid by weight.

15. An oxidation catalyst as recited in claim 13 wherein said liquid medium comprises an organic liquid medium.

* * * * *